(12) United States Patent
Butsev et al.

(10) Patent No.: US 7,835,892 B2
(45) Date of Patent: Nov. 16, 2010

(54) ULTRASOUND SIMULATION APPARATUS AND METHOD

(75) Inventors: Anton Butsev, Burke, VA (US); Weimin Wu, Boyds, MD (US)

(73) Assignee: Immersion Medical, Inc., Gaithersburg, MD (US)

( * ) Notice: Subject to any disclaimer, the term of this patent is extended or adjusted under 35 U.S.C. 154(b) by 696 days.

(21) Appl. No.: 10/950,776

(22) Filed: Sep. 28, 2004

(65) Prior Publication Data

US 2006/0069536 A1 Mar. 30, 2006

(51) Int. Cl.
- G06G 7/48 (2006.01)
- G06G 7/60 (2006.01)
- G06G 7/62 (2006.01)
- G09B 23/28 (2006.01)
- G09B 23/32 (2006.01)
- A61B 5/05 (2006.01)
- A61B 8/00 (2006.01)

(52) U.S. Cl. ............... 703/3; 703/11; 434/262; 434/267; 600/416; 600/437; 600/441

(58) Field of Classification Search ........... 600/416, 600/437, 441, 440, 458; 382/128, 276, 283; 703/1, 11, 3; 434/262, 267
See application file for complete search history.

(56) References Cited

U.S. PATENT DOCUMENTS

| | | | |
|---|---|---|---|
| 4,961,138 A | 10/1990 | Gorniak | |
| 5,088,046 A | 2/1992 | McMurtry | |
| 5,181,181 A | 1/1993 | Glynn | |
| 5,273,038 A | 12/1993 | Beavin | |
| 5,296,846 A | 3/1994 | Ledley | |
| 5,482,472 A | 1/1996 | Garoni et al. | |
| 5,546,943 A | 8/1996 | Gould | |
| 5,609,485 A * | 3/1997 | Bergman et al. | 434/262 |
| 5,724,264 A | 3/1998 | Rosenberg et al. | |
| 5,769,640 A | 6/1998 | Jacobus et al. | |
| 5,882,206 A | 3/1999 | Gillio | |
| 5,956,040 A | 9/1999 | Asano et al. | |
| 5,971,767 A | 10/1999 | Kaufman et al. | |
| 6,193,519 B1 | 2/2001 | Eggert et al. | |

(Continued)

FOREIGN PATENT DOCUMENTS

DE 102 58 952 A1 8/2004

(Continued)

OTHER PUBLICATIONS

Aiger et al. "Real-Time Ultrasound Imaging Simulation", 1998, 24 pages.*

(Continued)

*Primary Examiner*—Hugh Jones
*Assistant Examiner*—S Lo
(74) *Attorney, Agent, or Firm*—Kilpatrick Stockton, LLP

(57) ABSTRACT

A method includes receiving data values associated with one of a position and orientation of a simulated scanner relative to an object. Image values are calculated, substantially in real-time, based on the data values. A simulated ultrasound image is rendered in a graphical display based on the image values. The simulated ultrasound image is representative of an interior or a simulated interior of the object on the ultrasound scan plane.

19 Claims, 2 Drawing Sheets

U.S. PATENT DOCUMENTS

| | | | |
|---|---|---|---|
| 6,210,168 B1 * | 4/2001 | Aiger et al. | 434/262 |
| 6,623,433 B2 | 9/2003 | Webler et al. | |
| 6,726,638 B2 | 4/2004 | Ombrellaro | |
| 6,758,676 B2 * | 7/2004 | Eggert et al. | 434/262 |
| 2004/0009459 A1 * | 1/2004 | Anderson et al. | 434/262 |
| 2005/0271302 A1 * | 12/2005 | Khamene et al. | 382/294 |
| 2006/0064007 A1 * | 3/2006 | Comaniciu et al. | 600/416 |

FOREIGN PATENT DOCUMENTS

| | | |
|---|---|---|
| JP | H04-332544 | 11/1992 |
| JP | H07-171154 | 7/1995 |
| JP | 2002-336247 | 11/2002 |
| JP | 2003-061956 | 3/2003 |
| JP | 2003-067784 | 3/2003 |
| JP | 2003-319939 | 11/2003 |
| JP | 2004-070669 | 3/2004 |
| JP | 2004-070670 | 3/2004 |
| JP | 2004-159781 | 6/2004 |
| JP | 2004-171251 | 6/2004 |
| WO | WO 99/38141 * | 4/1999 |
| WO | WO 02/094080 A2 * | 11/2002 |

OTHER PUBLICATIONS

Maul et al. "Ultrasound simulators: experience with the SonoTrainer and comparative review of other training systems", Ultrasound Obstet Gynecol, Aug. 4, 2004, pp. 581-585.*

Cotin et al. "Real-Time Elastic Deformations of Soft Tissues for Surgery Simulation", IEEE Transactions of Visualization and Computer Graphics, vol. 5, No. 1, Jan.-Mar. 1999, pp. 62-73.*

Ehricke, Hans-Heino, "SONOSim3D: a multimedia system for sonography simulation and education with an extensible case database", European Journal of Ultrasound 7, 1998, pp. 225-230.*

Bates, Lisa M. et al., "A Method for Ultrasound Image Based Correction of Intraoperative Brain Shift," Proc. SPIE Medical Imaging 2000; Image Display and Visualization 3976: pp. 58-68.

Bro-Nielsen, Morten, "Finite Element Modeling in Surgery Simulation," Proceedings of the IEEE, vol. 86, No. 3, Mar. 1998, pp. 490-503.

Chen, Hongsheng et al., "Fast Voxelization of Three-Dimensional Synthetic Objects," Journal of Graphics Tools, vol. 3, No. 4, 1998, pp. 33-45.

Freidlin Raisa Z. et al., "NIHmagic: 3D Visualization, Registration and Segmentation Tool," 28th AIPR Workshop: 3D visualization for Data Exploration and Decision making, proc. Of SPIE vol. 3905, 2000, pp. 8 pages.

Hesina, Gerd et al, "Distributed Open Inventor: A Practical Approach to Distributed 3D Graphics," Vienna University of Technology, Austria, 1999, pp. 74-81.

Iwata, Hiroo et al., "Volume Haptization", Institute of Engineering Mechanics, 1993, pp. 16-23.

Kreeger, Kevin et al., "Mixing Translucent Polygons with Volumes, " Dept. of Computer Science, SUNY at Stony Brook, 1999, pp. 191-199.

Minsky, Margaret et al., "Feeling and Seeing: Issues in Force Display," Dept. of Computer Science, 1990, pp. 235-242, 270.

Stanley, Michael C. et al., "Computer Simulation of Interacting Dynamic Mechanical Systems Using Distributed Memory Parallel Processors," DSC-vol. 42, Advances in Robotics, ASME 1992, pp. 55-61.

Su, S. Augustine et al., "The Virtual Panel Architecture: A 3D Gesture Framework," Computer Science Department, 1993, pp. 387-393.

Weiler, Manfred et al., "Direct Volume Rendering in OpenSG," Computers & Graphics 28, 2004, pp. 93-98.

Weiskopf, Daniel et al., "Volume Clipping via Per-Fragment Operations in Texture-Based Volume Visualization," Visualization and Interactive Systems Group, 2002, pp. 93-100.

Westermann, Rudiger et al., "Efficiently Using Graphics Hardware in Volume Rendering Applications," Computer Graphics Proceedings, Annual Conference Series, 1998, pp. 169-177.

Yamakita, M. et al., "Tele Virtual Reality of Dynamic Mechanical Model," Proceedings of the 1992 IEEE/RSJ International Conference on Intelligent Robots and Systems, Jul. 7-10, 1992, pp. 1103-1110.

Written Opinion of the International Searching Authority for PCT/US2005/031391 received Mar. 1, 2006.

Office Action by UK Intellectual Property Office for application GB0706763.0, dated Oct. 26, 2009.

International Preliminary Report on Patentability for PCT/US2005/031391 dated Apr. 3, 2007.

Office Action dated May 11, 2010 in Japanese counterpart application 2007-533500, 2 pages.

English language translation of text of May 11, 2010 Office Action, 3 pages.

Office Action by UK Intellectual Property Office for application GB0706763.0, dated Jul. 1, 2010, 2 pages.

* cited by examiner

ULTRASOUND SIMULATION APPARATUS AND METHOD

BACKGROUND

The invention relates generally to graphical simulations, and more particularly to a method and apparatus for simulating an ultrasound image.

Ultrasound simulators allow medical professionals to gain experience using ultrasound equipment in a realistic environment without the need for live patients. Known ultrasound simulators have been developed that simulate the functionality of conventional ultrasound machines. In such simulators, a user manipulates a simulated ultrasound probe over a mannequin, while simultaneously viewing images captured from actual ultrasounds.

The images used in known ultrasound simulators are static images recorded from actual ultrasounds performed on live patients. Prior to the simulation, multiple images are taken at various depths and locations, and are cataloged for later retrieval during a simulation based on the manipulation of the simulated probe. The major drawback of these simulators is their inability to simulate dynamic situations (e.g., heart beat, breathing motions, palpation of organs, etc.). The static images are played back in the same manner regardless of the condition of the mannequin (i.e., whether or not the mannequin simulates breathing, a simulation user palpates the mannequin, etc.).

Other known simulators can produce independent static three-dimensional image models that are based on actual ultrasound images. The display of such models, however, is not based on use of an ultrasound simulator.

Thus, a need exists for an ultrasound simulation device and method that can produce ultrasound images based on dynamic models in real time.

SUMMARY OF THE INVENTION

A method is disclosed that includes receiving data values associated with a position of a simulated scanner relative to an object. Image values are calculated, substantially in real-time, based on the data values. A simulated ultrasound image is rendered in a graphical display based on the image values. The simulated ultrasound image is representative of an interior or a simulated interior of the object.

In other embodiments, a method includes rendering a first set of data values associated with a polygonal model to a stencil buffer of a graphics processor and rendering a second set of data values associated with the polygonal model to a frame buffer of the graphics processor. A set of pixel values is identified to represent one of an interior and a simulated interior of an object on an ultrasound scan plane using an exclusive or (XOR) algorithm. A simulated ultrasound image is rendered in a graphical display based on the data values rendered to the stencil buffer. The stencil buffer functions as a mask to actively assist rendering to the frame buffer only pixels representative of the interior or simulated interior of the object on the ultrasound scan plane.

DETAILED DESCRIPTION

A method is disclosed that includes receiving data values associated with a position of a simulated scanner relative to an object. Image values are calculated, substantially in real-time, based on the data values. A simulated ultrasound image is rendered in a graphical display based on the image values. The simulated ultrasound image is representative of an interior or a simulated interior of the object. The phrase "calculating substantially in real time" is used to describe the updating of simulated ultrasound images on a graphical display at a rate faster than the refresh rate of the simulation. Thus, the images are updated as the simulated scanner is passed over the object scanned, with little or no delay. The phrase "calculating substantially in real time" does not include, for example, loading a series of previously stored images from a database.

Additionally, the phrase "dynamically updated" refers to the updating of simulated ultrasound images in the graphical display based on manipulation of the object being "scanned" and/or the manipulation of the simulated scanner. Manipulation of the object being scanned can include, for example, palpating the object, the object simulating a physical deformation due to breathing simulation or pulse simulation, etc. Manipulation of the simulated scanner can include, for example, shaking the scanner, modifying the view angle of the scanner, etc.

Figure 1:
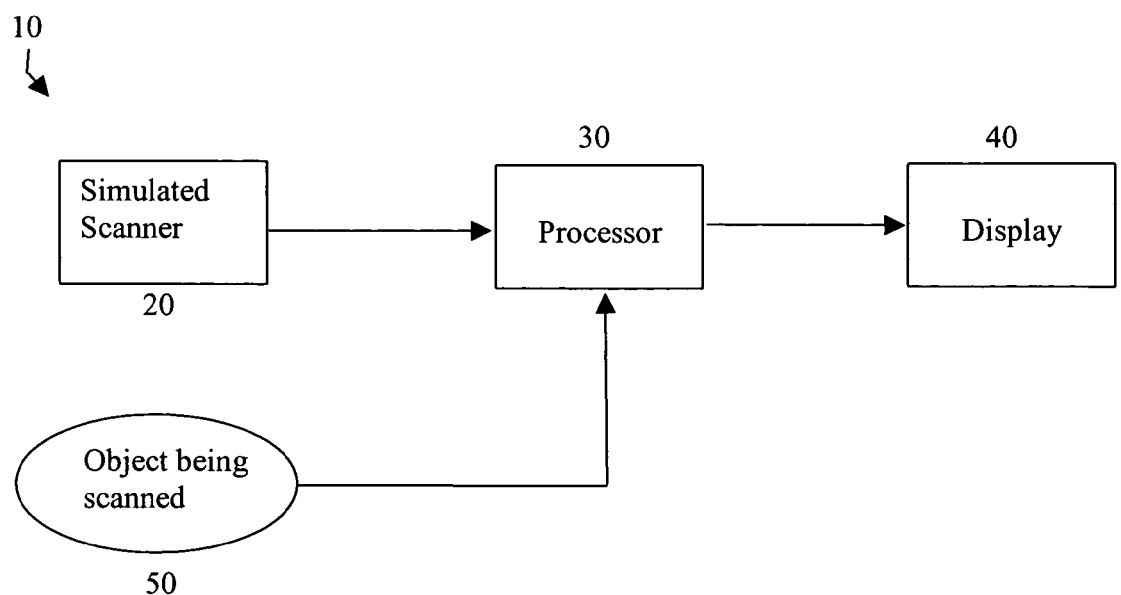
FIG. 1 is a schematic representation of an ultrasound simulation device according to an embodiment of the invention.

FIG. 1 is a schematic representation of an ultrasound simulation device according to an embodiment of the invention. The device 10 includes a simulated scanner 20 that is coupled to a processor 30. The processor 30 is configured to output signals to a display 40. An object 50 is coupled the processor 30 to send and receive signals based on the condition of the object 50 and the position of the scanner 20 relative to the object 50 as described below.

The simulated scanner 20 is "simulated" in the sense that it does not actually scan the object 50. As discussed in detail below, images on the display 40 are output based on a location of the simulated scanner 20 relative to the object 50 and not based on an actual scan of the object 50. In other words, while the simulated scanner 20 may be a functional ultrasound scanner in some embodiments, it does not perform a scanning function as part of the ultrasound simulation device 10. In other embodiments of the ultrasound simulation device, the simulated scanner 20 is a simulated scanner and is incapable of performing any scanning function regardless of the system with which it is used.

The object 50 can be representative of a portion of a body or an entire body. The object 50 may be an actual body part or a simulated body part. Regardless of whether the object 50 is an actual or simulated body part, object 50 does not affect the output from the processor 30 because object 50 is not actually scanned. The object 50 may be a mannequin or similar object shaped like a human. The output of a simulated ultrasound image on the display 40 is not dependent upon the shape or other physical characteristics of the object 50. In other words, the shape of the object need not be representative of a human body for the output to be a simulated representation of the interior of a human body.

Ultrasound simulation device 10 can have multiple modes of operation. In one embodiment, a single object 50 (e.g., a single box) may be used to represent multiple body parts. For example, in one mode of operation, the object 50 can represent an upper torso portion of a body and the displayed images can be associated with the interior of the upper torso (e.g., heart, lungs, etc.). In a second mode of operation, the object can represent a lower torso portion of a body and the displayed images are associated with the lower torso portion (e.g., the stomach, liver, etc.) accordingly. In other words, a single position on the object 50 can be associated with different images depending upon the operational mode of the ultrasound simulation device 10. In some embodiments, object 50 is not related to a body part. For example, object 50 can be a crate or a simulated crate that may contain real or simulated goods inside.

Figure 2:
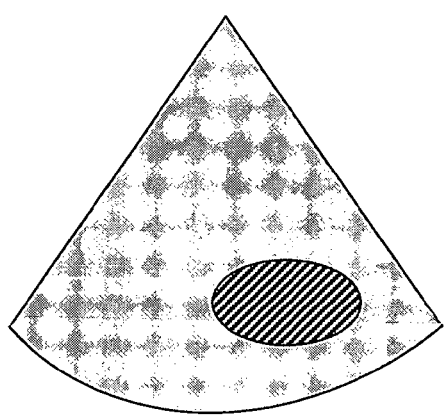
FIG. 2 is simulated image produced by an ultrasound simulation device according to an embodiment of the invention.

The display 40 is coupled to the processor 30 and is configured to output a simulated ultrasound image (see, e.g., FIG. 2) based on data values associated with a position of the simulated scanner 20 relative to the object 50. The processor 30 can be, for example, a commercially available personal computer or a less complex computing or processing device that is dedicated to performing one or more specific tasks. For example, the processor 30 can be a terminal dedicated to providing an interactive virtual reality environment, such as a gaming system, or the like.

The processor 30, according to one or more embodiments of the invention, can be a commercially available microprocessor. Alternatively, the processor 30 can be an application-specific integrated circuit (ASIC) or a combination of ASICs, which are designed to achieve one or more specific functions, or enable one or more specific devices or applications. In yet another embodiment, the processor 30 can be an analog or digital circuit, or a combination of multiple circuits.

The processor 30 includes a memory component (not shown in FIG. 1). The memory component can include one or more types of memory. For example, the memory component can include a read only memory (ROM) component and a random access memory (RAM) component. The memory component can also include other types of memory that are suitable for storing data in a form retrievable by the processor 30. For example, electronically programmable read only memory (EPROM), erasable electronically programmable read only memory (EEPROM), flash memory, as well as other suitable forms of memory can be included within the memory component. The processor 30 can also include a variety of other components, such as for example, co-processors, graphics processors, etc., depending upon the desired functionality of the device 10.

The processor 30 is in communication with the memory component, and can store data in the memory component or retrieve data previously stored in the memory component. The components of the processor 30 can communicate with devices external to the processor 30 by way of an input/output (I/O) component (not shown in FIG. 1). According one or more embodiments of the invention, the I/O component can include a variety of suitable communication interfaces. For example, the I/O component can include, for example, wired connections, such as standard serial ports, parallel ports, universal serial bus (USB) ports, S-video ports, large area network (LAN) ports, small computer system interface (SCSI) ports, and so forth. Additionally, the I/O component can include, for example, wireless connections, such as infrared ports, optical ports, Bluetooth® wireless ports, wireless LAN ports, or the like.

The processor 30 is configured to send and receive signals to and from the object 50 and the simulated scanner 20. The processor 30 receives data values associated with the position of the simulated scanner 20 relative to object 50. The position signals can be received from either the simulated scanner 20 or the object 50. The position of the simulated scanner 20 can be measured, for example, as a relative distance and direction from a predetermined reference point. The reference point can be a point on or in the object 50 or some other location in the device 10. For example, if the object 50 is configured to be positioned on a support (not shown), the reference point can be on the support. In alternative embodiments, a sensor or multiple sensors (not shown) can be disposed in the object that are configured to detect the location of the simulated scanner 20 with respect to the object 50. Alternatively, the object 50 can include a wireless or wired transmitter (not shown) that sends a position signal to the simulated scanner 20 to determine position information of the simulated scanner 20 relative to the object 50.

It is desirable for the position of the simulated scanner 20 relative to the object 50 to be coordinated in a realistic sense with respect to the images output on the display 40. For example, when the object is a simulated human body, the images output on the display 40 should be the relevant portion of the interior of the body corresponding to the position of the scanner 20 (e.g., when the simulated scanner 20 is positioned above the simulated location of the heart, an image of a heart is output on the display 40).

As the simulated scanner 20 is moved from one position to another, the images output on the display 40 are dynamically updated substantially in real time as will be described below. In some embodiments of the invention, the simulated scanner 20 is provided in a fixed location and the object 50 is movable with respect to the simulated scanner 20. When movement of the simulated scanner 20 is discussed herein, the movement is a relative movement with respect to the object 50. Movement of the object 50 relative to the simulated scanner 20 provides output similar to the output produced when the simulated scanner 20 moves.

The processor 30 is capable of calculating, substantially in real time, image values based on the data values associated with the position of the simulated scanner 20 relative to the object 50. The simulated ultrasound image is rendered graphically on the display 40 based on the calculated image values. The simulated ultrasound image is representative of an interior or a simulated interior of the object 50 on the ultrasound scan plane. In other words, where the displayed simulated ultrasound image represents an actual interior of the object 50 being used with the ultrasound simulation device 10, then the simulated ultrasound image is representative of the actual interior of the object 50.

Figure 3:
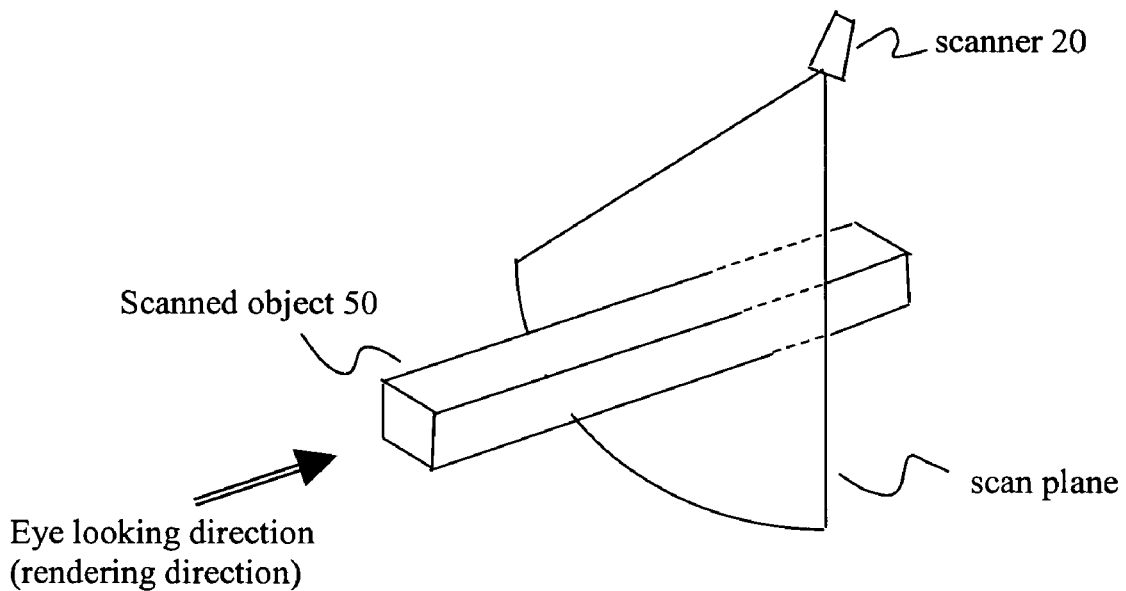
FIG. 3 illustrates a scan plane and a rendering direction defined by a scanner position and orientation relative to a scanned object according to an embodiment of the invention.

Referring to FIG. 3, when the simulated scanner 20 is positioned adjacent the object 50, a scan plane is defined based on at least one of the position and orientation of scanner 20 relative to the object 50. During the process of rendering an image to the stencil buffer or the frame buffer, the rendering direction is defined as being substantially perpendicular to the ultrasound scan plane.

Figure 4:
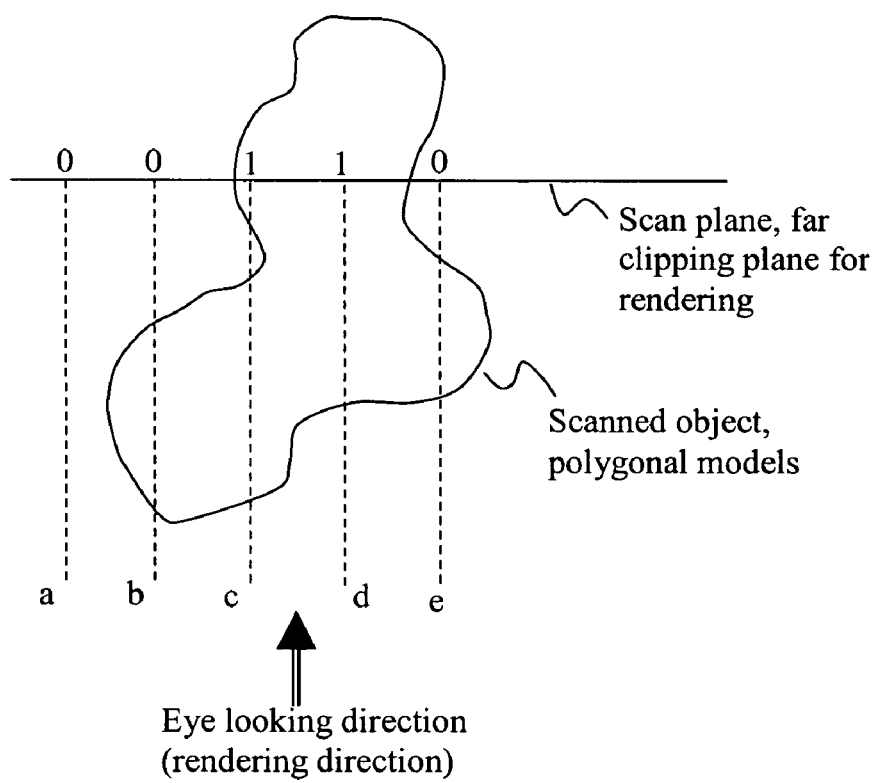
FIG. 4 is an example of applying an Exclusive Or (XOR) algorithm to render an image to a stencil buffer.

The rendering of simulated ultrasound images can first be performed by a stencil buffer algorithm based on a computer graphics language, for example, Open GL or DirectX. FIG. 4 illustrates how the Exclusive Or (XOR) stencil buffer algorithm can identify the pixels that represent an interior of a scanned object on the scan plane. Some polygonal models representing scanned objects are stored in processor 30. When the scan plane is used as the far clipping plane to render to models to the stencil buffer using an XOR algorithm, only those pixels that represent the interior of the scanned object on the scan plane will be written an odd number of times. Referring to FIG. 4, for example, the pixels in the stencil buffer corresponding to lines a, b, c, d, e are written 0, 2, 3, 1, 2 times, respectively. Since pixels c and d are written an odd number of times, they are identified as among the interior pixels of the scanned object on the scan plane.

Various polygonal models corresponding to the displayed image are defined such that the simulated scanner 20 is perpendicular to a cutting plane (i.e., the plane parallel to the scan plane) of the object 50. The polygonal models are rendered to a stencil buffer with, for example, stencil buffer settings:

glClearStencil(0x0);
glClear(GL_STENCIL_BUFFER_BIT);
glStencilFunc(GL_NEVER, 0x1, 0x1);
glStencilOp(GL_INVERT, GL_KEEP, GL_KEEP).

Pixels that are represented as a cross section (i.e., have a visible portion of the scanned simulated interior of object 50) have a value of "1" in the stencil buffer matrix.

Next, the polygonal models are rendered to a frame buffer with the stencil buffer enabled as a mask. Any pixel with a stencil buffer value of 1 can be written and any pixel with a stencil buffer value of 0 is masked or blocked from being written. An ultrasound texture can be used with this round of rendering to give the rendered image a more realistic appearance. The texture can be captured, for example, from actual ultrasound images. The stencil buffer is enabled with, for example, the settings:

GlEnable(GL_STENCIL_TEST);
glStencilFunc(GL_NOTEQUAL, 0x0, 0x1);
glStencilOp(GL_KEEP, GL_KEEP, GL_KEEP).

The ultrasound fan-shaped mask is then drawn to the stencil buffer and the frame buffer based on the calculations of the interior and the boundary of the displayed image.

Using the method described above, substantially real-time updates of the simulated ultrasound image are rendered. As the position of the simulated scanner 20 changes, the image dynamically changes. Additionally, the position of the simulated scanner 20 can be maintained while the image is dynamically updated based on movement of the object 50 or simulated movement of the object 50. For example, a mannequin representing a human body can be configured to simulate human breathing and cardiac functions. Thus, when the heart or lungs are being scanned, the simulated ultrasound image will change with the simulated movement of the scanned moving organ even though the position of the simulated scanner 20 does not change with respect to the object 50.

Additionally, the object 50 can be physically moved. For example, if the object 50 is being used as a palpation simulator, when a user pushes down on the object 50, the simulated organ being scanned can change in shape. Accordingly, the simulated ultrasound image is updated based on the change in distance between the object 50 and the simulated scanner 20. Palpation simulators incorporating haptic feedback devices are described in U.S. application Ser. No. 09/848,966, filed May 4, 2001, which is incorporated herein by reference in its entirety.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalence.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention.

For example, although the simulated scanner 20 is illustrated as being external to the object 50, in an alternative embodiment the simulated scanner can be an internal scanner and can be inserted in the object.

Although the processor 30 is described above as being directly coupled to the simulated scanner 20 and the simulated body part, in an alternative embodiment, the processor can be coupled to the ultrasound simulation device 10 via a network.

Although the device as described above is used with a simulated body part, in an alternative embodiment, the device is used for simulated scanning of objects such as boxes, crates, etc.

What is claimed is:

1. A method comprising:
    placing a first physical object and a simulated scanner in contact with one another, the first physical object representing an object to be a subject of a simulated scan during an ultrasound simulation, the contact between the first physical object and simulated scanner established at least once during the simulation, wherein the simulated scanner is a second physical object;
    during the simulation, rendering a simulated ultrasound image of the first physical object based on a position of the simulated scanner during the simulation without the simulated scanner scanning the first physical object;
    while the first physical object and simulated scanner are in contact, detecting a change in position of the simulated scanner relative to a reference point using at least one sensing device and receiving a plurality of data values, wherein the change in position of the simulated scanner is caused by a movement of the first physical object occurring during the simulation;
    calculating, substantially in real-time, a plurality of image values based on the plurality of data values; and
    updating based on the plurality of image values at least a portion of the simulated ultrasound image of the first physical object, the plurality of data values associated with a polygonal model of the first physical object.

2. The method of claim 1, wherein the updating includes rendering at least a portion of a simulated ultrasound image via a stencil buffer algorithm.

3. The method of claim 1, wherein one of the position and orientation of the simulated scanner relative to the first physical object defines a scan plane and a rendering direction.

4. The method of claim 2, wherein the rendering the simulated ultrasound image includes rendering a first set of data values from the plurality of data values to a stencil buffer of a graphics processor, and rendering a second set of data values from the plurality of data values to a frame buffer of the graphics processor, the first set of data values and the second set of data values being associated with a polygonal model of the first physical object.

5. A method comprising:
    placing a first physical object and a simulated scanner in contact with one another, the first physical object representing an object to be a subject of a simulated scan during an ultrasound simulation, the contact between the first physical object and simulated scanner established at least once during the simulation and wherein the simulated scanner is a second physical object;

during the simulation, detecting a change in position of a simulated scanner using at least one sensing device without the simulated scanner scanning the first physical object;
receiving a first set of data values and a second set of data values, wherein at least one of the first set and second set of data values indicates the change in position of the simulated scanner relative to a reference point, the change in position being caused by movement of the first physical object during the simulation;
rendering the first set of data values to a stencil buffer of a graphics processor;
rendering the second set of data values to a frame buffer of the graphics processor; and
applying an exclusive or (XOR) to the first set of data values to identify a set of pixel values associated with one of an actual interior or simulated interior of an object on an ultrasound scan plane, the first set of data values and the second set of data values being associated with a polygonal model of the first physical object.

6. The method of claim 5, wherein the XOR is applied to the first set of data values and the second set of data values via a stencil buffer algorithm.

7. The method of claim 5, wherein the first set of data values and the second set of data values are based on at least one of a position and an orientation of the simulated scanner with respect to the first physical object.

8. The method of claim 5, the first physical object comprising a simulated body part.

9. The method of claim 5, further comprising:
updating the first set of data values and the second set of data values based on a movement of the first physical object.

10. The method of claim 9, the first physical object comprising a simulated body part, wherein the movement is a simulated movement based on a physiological property of the simulated body part.

11. A method comprising:
placing a first physical object and a simulated scanner in contact with one another, the first physical object representing an object to be a subject of a simulated scan during an ultrasound simulation during which the simulated scanner does not scan the first physical object, the contact between the first physical object and simulated scanner established at least once during the simulation and wherein the simulated scanner is a second physical object;
using at least one sensing device, detecting a change in position of a simulated scanner relative to a reference point;
receiving a first set of data values identifying the change of position, the change of position occurring while providing a simulated ultrasound image of a first physical object, the change in position being caused by a movement of the first physical object during the simulation, the simulated scanner in contact with the first physical object at least when the movement occurs;
receiving a second set of data values identifying the change in position of the simulated scanner relative to the reference point, the second set of data values different from the first set of data values;
applying via a stencil buffer algorithm an exclusive or (XOR) to the first set of data values and the second set of data values to identify a set of pixel values associated with one of an actual interior or a simulated interior of the first physical object;
rendering a polygonal model associated with the first set of data values to a stencil buffer; and
rendering the polygonal model associated with the second set of data values to a frame buffer.

12. The method of claim 11, wherein the rendering the polygonal model to the frame buffer includes using the stencil buffer as a mask.

13. A processor-readable medium storing code representing instructions to cause a processor to simulate ultrasound imaging of an object, the code comprising code to:
render a simulated ultrasound image of a first physical object based on a position of a simulated scanner during a simulation relative to the first physical object, the simulated scanner in contact with the first physical object at least once during the simulation, wherein the simulated scanner is a second physical object that does not scan the first physical object during the simulation;
detect a change in position of the simulated scanner relative to a reference point using at least one sensing device;
receive a plurality of data values indicating the change in position of the simulated scanner relative to the reference point, wherein the change in position of the simulated scanner is caused by a movement of the first physical object during the simulation while the first physical object and simulated scanner are in contact;
calculate, substantially in real-time, a plurality of image values associated with a polygonal model of the object based on the plurality of data values; and
update based on the plurality of image values at least a portion of the simulated ultrasound image of the first physical object.

14. The processor-readable medium of claim 13, wherein the code to update at least a portion of the simulated ultrasound image further comprises code to:
render a first set of data values from the plurality of data values to a stencil buffer of a graphics processor;
render a second set of data values from the plurality of data values to a frame buffer of the graphics processor; and
apply via a stencil buffer algorithm an exclusive or (XOR) to the first set of data values and second set of data values to identify a set of pixel values associated with one of a simulated interior and an actual interior of the first physical object.

15. A processor-readable medium storing code representing instructions to cause a processor to simulate ultrasound imaging of a first physical object, the code comprising code to:
detect a change in position of a simulated scanner relative to a reference point using at least one sensing device, wherein the simulated scanner is a second physical object that does not scan the first physical object during the simulation;
receive a first set of data values and a second set of data values, wherein at least one of the first set and second set of data values indicates a change in position of a simulated scanner relative to the reference point, the change in position being caused by a movement of the first physical object during the simulation and while the simulated scanner is in contact with the first physical object;
render the first set of data values to a stencil buffer of a graphics processor;
render the second set of data values to a frame buffer of the graphics processor; and
apply an exclusive or (XOR) to the first set of data values to identify a set of pixel values associated with one of an actual interior and simulated interior of an object on an ultrasound scan plane, the first set of data values and the second set of data values being associated with a polygonal model of the first physical object.

16. The processor-readable medium of claim 15, further comprising code to:
update the first set of data values and second set of data values based on a movement of the first physical object.

17. The processor-readable medium of claim 15, the first physical object comprising a simulated body part, the code further comprising code to:
update the first set of data values and the second set of data values based on a movement based on a physiological property of the simulated body part.

18. The processor-readable medium of claim 15, further comprising code to:
update the first set of data values and the second set of data values based on manipulation of the first physical object.

19. The method of claim 1, wherein the reference point includes one of:
a reference point located on the first physical object,
a reference point located in the first physical object, or
a reference point located apart from the first physical object.

* * * * *